United States Patent
Zhang et al.

(10) Patent No.: US 11,975,315 B2
(45) Date of Patent: May 7, 2024

(54) METHOD FOR PARTIALLY REGENERATING CATALYST FOR METHANOL AND/OR DIMETHYL ETHER-TO-OLEFIN AND METHOD FOR METHANOL AND/OR DIMETHYL ETHER-TO-OLEFIN

(71) Applicant: DALIAN INSTITUTE OF CHEMICAL PHYSICS, CHINESE ACADEMY OF SCIENCES, Dalian (CN)

(72) Inventors: Jinling Zhang, Dalian (CN); Mao Ye, Dalian (CN); Zhongmin Liu, Dalian (CN); Jibin Zhou, Dalian (CN); Tao Zhang, Dalian (CN); Xiangao Wang, Dalian (CN); Hailong Tang, Dalian (CN); Jing Wang, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 263 days.

(21) Appl. No.: 17/609,764

(22) PCT Filed: May 10, 2019

(86) PCT No.: PCT/CN2019/086394
§ 371 (c)(1),
(2) Date: Nov. 8, 2021

(87) PCT Pub. No.: WO2020/227849
PCT Pub. Date: Nov. 19, 2020

(65) Prior Publication Data
US 2022/0274099 A1      Sep. 1, 2022

(51) Int. Cl.
*B01J 38/06* (2006.01)
*B01J 29/85* (2006.01)
(Continued)

(52) U.S. Cl.
CPC .............. *B01J 38/06* (2013.01); *B01J 29/85* (2013.01); *B01J 29/90* (2013.01); *C07C 1/20* (2013.01)

(58) Field of Classification Search
None
See application file for complete search history.

(56) References Cited

U.S. PATENT DOCUMENTS

| 6,965,057 B2 | 11/2005 | Beech, Jr. et al. |
| 2006/0135836 A1* | 6/2006 | Beech ............... C10G 3/49 502/41 |

(Continued)

FOREIGN PATENT DOCUMENTS

| EA | 005667 B1 | 4/2005 |
| EA | 010038 B1 | 6/2008 |

OTHER PUBLICATIONS

Extended Search Report dated Apr. 21, 2022 issued in corresponding European Application No. 19928705.3.
(Continued)

*Primary Examiner* — Tam M Nguyen
(74) *Attorney, Agent, or Firm* — Nath, Goldberg & Meyer; Joshua B. Goldberg

(57) ABSTRACT

Disclosed is a method for partially regenerating a catalyst for methanol and/or dimethyl ether-to-olefin. The method comprises: introducing a mixed gas into a regenerated region containing a catalyst to be regenerated, and subjecting same to a partial regeneration reaction to obtain a regenerated catalyst, wherein the mixed gas contains water vapor and air; and in the regenerated catalyst, the coke
(Continued)

content of at least part of the regenerated catalyst is greater than 1%. The method utilizes the coupling of a mixed gas of water vapor and air to activate a deactivated catalyst, selectively eliminate part of a coke deposit in the catalyst to be regenerated, and obtain a partially regenerated catalyst for methanol-to-olefin. Another aspect of the present invention is that further provided is a method for methanol and/or dimethyl ether-to-olefin by using the partially regenerated catalyst for methanol-to-olefin regenerated by means of the method.

9 Claims, 7 Drawing Sheets

(51) Int. Cl.
*B01J 29/90* (2006.01)
*C07C 1/20* (2006.01)

(56) References Cited

U.S. PATENT DOCUMENTS

2013/0225895 A1* 8/2013 Quevedo Enriquez .. B01J 29/06
585/653
2013/0225896 A1* 8/2013 Chewter ................... C07C 1/22
585/653

OTHER PUBLICATIONS

Zhou, et al., "Partial Regeneration of the Spent SAPO-34 Catalyst in the Methanol-to-Olefins Process via Steam Gasification", Ind. Eng. Chem. Res., vol. 57, No. 51, pp. 17338-17347, 2018.
Tian, et al., "Methanol to Olefins (MTO): From Fundamentals to Commercialization", ACS Catalysis, vol. 5, No. 3, pp. 1922-1938, 2015.

* cited by examiner

METHOD FOR PARTIALLY REGENERATING CATALYST FOR METHANOL AND/OR DIMETHYL ETHER-TO-OLEFIN AND METHOD FOR METHANOL AND/OR DIMETHYL ETHER-TO-OLEFIN

This is a National Phase Application filed under 35 U.S.C. 371 as a national stage of PCT/CN2019/086394, filed May 10, 2019, the content of which is hereby incorporated by reference in its entirety.

FIELD

The present application relates to a method for partially regenerating a catalyst for methanol and/or dimethyl ether-to-olefin, and a method for methanol and/or dimethyl ether-to-olefin. The present application belongs to the field of chemical catalysts.

BACKGROUND

Ethylene and propylene are important basic raw materials for the national economy and play an important strategic position in the development of petrochemical and chemical industries. The raw material of ethylene production in our country is mainly naphtha, which has a relatively high cost. Industrially, methanol-to-olefins technology, using coal, SAPO catalysts, and fluidized bed technology, has successfully produced light olefins with high selectivity. However, after a period of reaction of the SAPO catalyst, coke deposition leads to deactivation, and it needs to be regenerated by burning coke to restore the activity and selectivity of the catalyst.

In the prior art, the regeneration process of the coked catalyst for methanol-to-olefins uses air-based mixed gas as regeneration gas, and the amount of auxiliary gas in the regeneration feed gas is adjusted to prevent "temperature runaway" or "tail combustion" phenomenon during the regeneration process.

However, this process produces a large amount of greenhouse gas $CO_2$, which is not conducive to environmental protection and reduces the utilization ratio of carbon atoms of methanol. In addition, if coke combustion with air is used to partially regenerate the catalyst, the rate of coke combustion is relatively fast, which is not conducive to control the residual coke amount of the catalyst and increases the difficulty in the operation process.

SUMMARY

According to one aspect of the present application, a method for partially regenerating a catalyst for methanol and/or dimethyl ether-to-olefin is provided. The method utilizes the mixed gas of water vapor and air to activate a deactivated catalyst and selectively remove partial coke deposited on the deactivated catalyst, to obtain partially regenerated catalyst for methanol-to-olefin with higher olefin selectivity.

The method for partially regenerating a catalyst for methanol and/or dimethyl ether-to-olefin is characterized in that the method comprises: passing a mixed gas into a regeneration zone containing the catalyst to be regenerated, and performing partial regeneration reaction to obtain the regenerated catalyst;

wherein, the mixed gas comprises water vapor and air; and for the regenerated catalyst, at least a part of the regenerated catalyst has a coke content of greater than 1%.

By mixing air and water vapor, the method uses the fluidity of air to increase the selectivity of water vapor for the removal of coke deposits near the active site and further increase the catalytic activity. The obtained partially regenerated catalyst has higher selectivity to light olefins, and meanwhile maintains higher methanol conversion ratio.

When only air is used for regeneration (or when the proportion of air is high during regeneration), the regeneration rate is fast. Partial regeneration of the catalyst through coke combustion with air will greatly change the property of the residual coke deposited on the catalyst. The regenerated catalyst containing such residual coke weakens the catalytic activity during the reaction, resulting in the selectivity of light olefins not reaching the maximum. When only water vapor is used for regeneration, the property and content of residual coke deposited on catalyst can be well adjusted by controlling the conditions such as reaction temperature, space velocity and reaction time, to ensure and enhance the selectivity of light olefins in the product. However, due to the weak oxidation capacity of water vapor, high regeneration temperature and long regeneration time is required, which may easily cause the accumulation of coke, leading to unsatisfactory regenerated life.

Specifically, for the mixed gas of water vapor and air in which air proportion is lower, the advantages of these two gases can simultaneously work, and their disadvantages can be complemented. It avoids the large amount of greenhouse gas $CO_2$ produced in the traditional non-selective deep coke combustion with air, and at the same time, the partially regenerated catalyst can enhance the selectivity of olefins in the MTO reaction product and improve the economy of MTO.

The catalyst treated by this method can span or shorten the induction period that a fresh catalyst or a fully regenerated catalyst must go through, so that the catalyst is always in the best performance state. At the same time, due to the control of the property of the residual coke deposited on catalyst, proportion of light olefins can be adjusted to improve the economy of methanol to olefins.

Optionally, a volume ratio of water vapor to air in the mixed gas ranges from 1:0.001 to 1:0.8.

Preferably, the volume ratio of water vapor to air in the mixed gas ranges from 1:0.01 to 1:0.5.

Further preferably, the volume ratio of water vapor to air in the mixed gas ranges from 1:0.01 to 1:0.14.

Optionally, in the partial regeneration reaction, the contact time between the mixed gas and the catalyst to be regenerated ranges from 10 min to 200 min.

Optionally, at least a part of the regenerated catalyst has the coke content ranging from 1.1% to 8%.

Preferably, the coke content of the regenerated catalyst obtained after the partial regeneration reaction in the regenerator ranges from 2.8% to 7.5%. The coke content of the regenerated catalyst mentioned herein refers to the coke content of the entire regenerated catalyst.

The lower limit of the coke content of the regenerated catalyst obtained after the partial regeneration reaction in the regenerator is 1.2%, 1.5%, 1.6%, 1.7%, 1.8%, 2%, 2.94%, 3%, 3.89% or 4%, and the upper limit thereof is 2%, 2.94%, 3%, 3.89%, 4%, 4.7%, 5.1%, 5.9%, 6%, 7% or 8%.

Further preferably, the coke content of the regenerated catalyst obtained after the partial regeneration reaction in the regenerator ranges from 1.6% to 7%.

In the present application, the calculation formula for the coke content ω of the catalyst is shown in the following formula I:

$$\text{Coke content } \omega = (m_{250°C} - m_{900°C})/m_{250°C} \times 100\% \quad \text{Formula I}$$

In formula I, ω is the coke content of the catalyst in weight percentage, $m_{250°C}$ is the weight of the catalyst when the temperature is raised from room temperature to 250° C. in the air atmosphere, and $m_{900°C}$ is the weight of the catalyst when the temperature is raised to 900° C.

Optionally, the space velocity of water vapor in the mixed gas passed into the regenerator ranges from 0.1 h$^{-1}$ to 10 h$^{-1}$, and the space velocity of air ranges from 0.01 h$^{-1}$ to 6 h$^{-1}$.

Optionally, the partial regeneration reaction is carried out under a temperature ranging from 500° C. to 700° C.

Preferably, the partial regeneration reaction is carried out under the temperature ranging from 600° C. to 680° C.

Optionally, the coke content of the catalyst to be regenerated ranges from 6% to 14%.

Optionally, the catalyst is used for methanol-to-olefins reaction in a fluidized bed reactor, the deactivated catalyst for methanol-to-olefins is transported to the regenerator for partial regeneration reaction, and the regenerated catalyst obtained is partially regenerated catalyst. Partially regenerated catalyst is recycled back to the fluidized bed reactor.

The catalyst for methanol-to-olefins is the silicoaluminophosphate molecular sieve.

The catalyst for methanol-to-olefin is a fluidized bed catalyst.

In the present application, "olefin" refers to ethylene and propylene.

According to another aspect of the present application, this provides a method for methanol and/or dimethyl ether-to-olefin, which adopts a fluidized bed reaction process and partially regenerates the catalyst to be regenerated according to the above-mentioned method for partially regenerating the catalyst for methanol to olefins.

Optionally, the feed gas comprising methanol and/or dimethyl ether is passed into a fluidized bed reactor containing a catalyst to perform methanol-to-olefins reaction;
    the catalyst to be regenerated is transported to the regeneration zone, and the mixed gases are passed into the regeneration zone to perform partial regeneration reaction to obtain the regenerated catalyst;
    the regenerated catalyst is recycled back to the fluidized bed reactor.

Optionally, the catalyst for methanol-to-olefins is silicoaluminophosphate molecular sieve.

The beneficial effects that the present application can achieve include:

1) The catalyst is partially regenerated by gasifying coke deposited on the catalyst with the mixed gas of water vapor and air as the regeneration gas, and the gasification products are mainly CO and $H_2$, which can be recycled, and the utilization ratio of carbon atoms of methanol can be improved.

2) By adjusting the ratio of water vapor to air, their advantages can work respectively, which is beneficial to the control of the property and content of the residual coke deposited on catalyst. The coke gasification using water vapor needs to be near the active site of the catalyst, while a small amount of air can speed up the transformation of coke at the active site, thereby selectively removing coke content.

3) When the partially regenerated catalyst obtained using the mixed gas of water vapor and air is used to MTO reaction, the initial selectivity of light olefin is increased from about 62% which is achieved over the fully regenerated catalyst, to the range from 65% to 83%, and further the highest selectivity is ensured.

4) When the partially regenerated catalyst obtained using the mixed gas of water vapor and air is used to perform MTO reaction, the methanol as reactant is almost completely converted, which is the same as that of the fresh catalyst and is close to 100%.

DETAILED DESCRIPTION

The present application will be described in detail below with reference to the examples, but the present application is not limited to these examples.

The catalyst used in the present application is the commercially available catalyst for methanol-to-olefins.

The method for determining the coke content of the catalyst is as follows.

The catalyst is heated to 250° C. in air atmosphere, and the weight is denoted as $m_{250°C}$; and the catalyst is heated to 900° C. in air atmosphere, and the weight is denoted as $m_{900°C}$. The coke content of the catalyst is determined by the following formula I:

$$\text{Coke content } \omega = (m_{250°C} - m_{900°C})/m_{250°C} \times 100\% \quad \text{Formula I}$$

The methanol conversion ratio, ethylene selectivity and propylene selectivity in the examples are all calculated based on the number of carbon moles.

In the examples, the XRD characterization of the sample adopts a Philips X'Pert PROX X-ray diffractometer, a copper target, and $K_\alpha$ radiation source ($\lambda$=1.5418 Å). The working voltage of this instrument is 40 kV and the working current is 40 mA.

Figure 1:
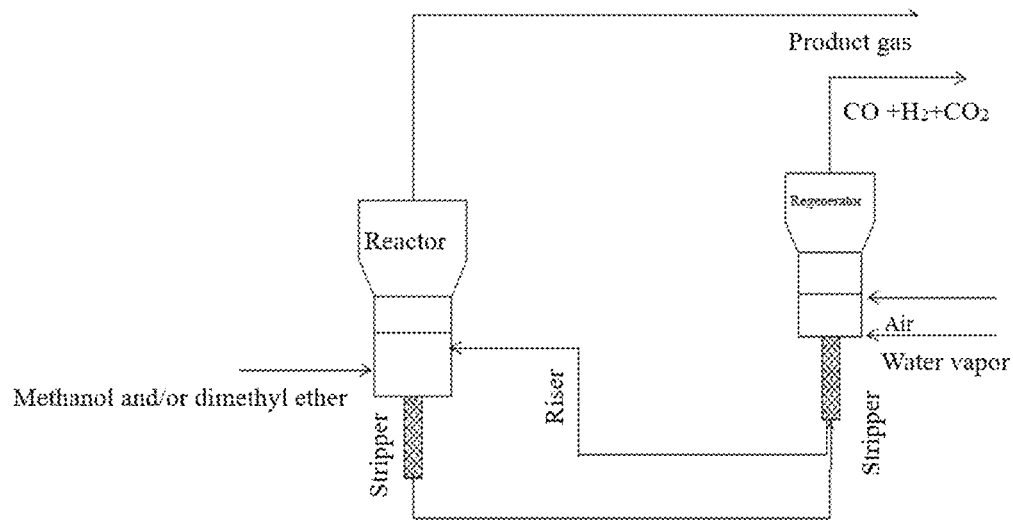
FIG. 1 is a schematic diagram of a method for partially regenerating the catalyst with the mixed gases of water vapor and air according to the present invention.

FIG. 1 is a process route diagram of methanol-to-olefins, which adopts the method for partially regenerating the catalyst for methanol-to-olefins described in the present application. Specifically, the raw materials comprising methanol and/or dimethyl ether are passed into the reactor, and the product gas (ethylene and propylene) after the reaction leaves from the top of the reactor. The deactivated catalyst enters the catalyst regenerator through the stripper, and the mixed gas of air and water vapor in a specific proportion is introduced to the catalyst regenerator to perform partial regeneration reaction of the deactivated catalyst. The generated CO, $H_2$, and $CO_2$ leave the catalyst regenerator, and the regenerated catalyst is returned to the reactor through the riser.

Example 1

4 g commercially used catalyst for methanol-to-olefins, with the active component SAPO-34, denoted as DMTO-1, was loaded to a fixed fluidized bed reactor to perform methanol-to-olefins reaction. The raw materials for methanol-to-olefins reaction were 80 wt % methanol aqueous solution. The reaction temperature was 490° C., the pressure was 0.1 MPa, and the space velocity of methanol was 2.1 $h^{-1}$. The reaction time was 107 min, and the methanol conversion ratio and olefin selectivity were shown in FIG. 2.

The catalyst obtained after the above reaction ends was denoted as "deactivated catalyst A". It was determined that the coke content of the deactivated catalyst A is 10.2%.

Comparative Example 1

The deactivated catalyst A was calcined in a muffle furnace at 600° C. for 6 hours to obtain a fully regenerated catalyst, which was denoted as sample D1#. It was determined that the coke content of the sample D1# is 0.05%.

According to reaction conditions of the methanol-to-olefins in Example 1, the methanol-to-olefins reaction was performed on the regenerated catalyst sample D1#. The reaction time was 89 min, and the methanol conversion ratio and olefin selectivity were shown in FIG. 3.

Example 2

The deactivated catalyst A was placed in the reactor, and the reactor was purged with nitrogen at a flow rate of 100 mL/min. The reactor was heated to 650° C. for 10 min, and then the feeding of nitrogen was stopped. Then water vapor and air were passed to the reactor for 20 minutes, wherein the volume ratio of water vapor to air was 1:0.4, the weight hourly space velocity of water vapor was 8 $h^{-1}$, and the weight hourly space velocity of air was 4.8 $h^{-1}$. It was determined that the coke content of the obtained catalyst had is 1.2%.

The reactor was switched to be nitrogen gas atmosphere, the temperature therein was reduced to 490° C. and maintained for 20 min to obtain the partially regenerated catalyst, which was denoted as sample 1#.

According to reaction conditions of methanol-to-olefins in Example 1, the methanol-to-olefins reaction was performed on the partially regenerated catalyst sample 1#. The reaction time was 72 min, and the methanol conversion ratio and olefin selectivity were shown in FIG. 4.

Example 3

The deactivated catalyst A, which was obtained according to the method of Example 1, was placed in the reactor, and the reactor was purged with nitrogen at a flow rate of 100 mL/min. The reactor was heated to 680° C. for 10 min, and then the feeding of nitrogen was stopped. Then water vapor and air were passed to the reactor for 180 min, wherein the volume ratio of water vapor to air was 1:0.02, the weight hourly space velocity of water vapor was 2 $h^{-1}$, and the weight hourly space velocity of air was 0.06 $h^{-1}$. It was determined that the coke content of the obtained catalyst is 1.6%.

The reactor was switched to be nitrogen atmosphere, the temperature therein was reduced to 490° C. and maintained for 20 min to obtain the partially regenerated catalyst, which was denoted as sample 2#.

Figure 5:
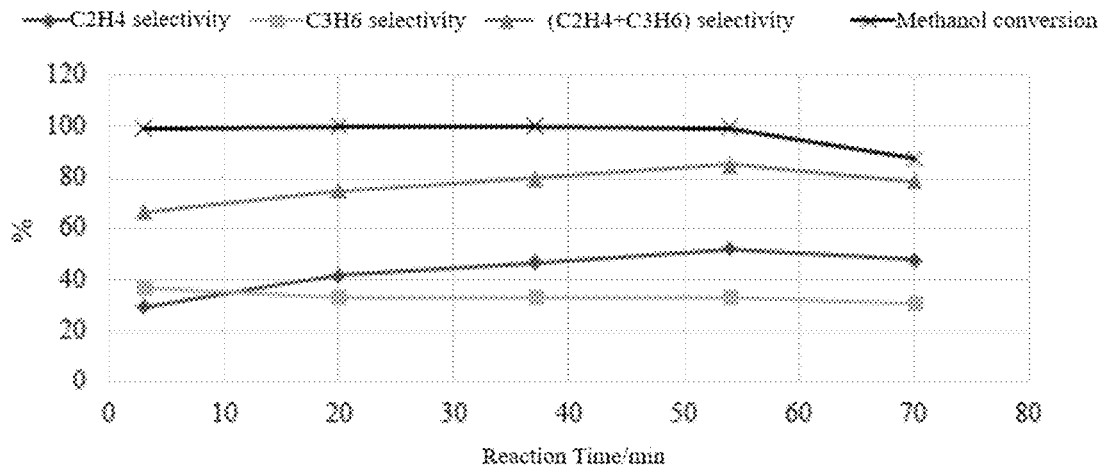
FIG. 5 is a schematic diagram showing the catalytic performance of sample 2[#] according to Example 3 of the present application.

According to reaction conditions of methanol-to-olefins in Example 1, the methanol-to-olefins reaction was performed on the partially regenerated catalyst sample 2#. The reaction time was 72 min, and the methanol conversion ratio and olefin selectivity are shown in FIG. 5.

Example 4

The deactivated catalyst A, which was obtained according to the method of Example 1, was placed in the reactor, and the reactor is purged with nitrogen at a flow rate of 100 mL/min. The reactor was heated to 620° C. for 10 min, and then the feeding of nitrogen was stopped. Then water vapor and air were passed to the reactor for 60 min, wherein the volume ratio of water vapor to air was 1:0.14, the weight hourly space velocity of water vapor was 3 $h^{-1}$, and the weight hourly space velocity of air was 0.63 $h^{-1}$. It was determined that the obtained catalyst had a coke content of 2.8%.

The reactor was switched to be nitrogen atmosphere, the temperature therein was reduced to 490° C. and maintained for 20 min to obtain the partially regenerated catalyst, which was denoted as sample 3#.

According to reaction conditions of methanol-to-olefins in Example 1, the methanol-to-olefins reaction was performed on the partially regenerated catalyst sample 3#. The reaction time was 72 min, and the methanol conversion ratio and olefin selectivity were shown in FIG. 6.

Example 5

The deactivated catalyst A, which was obtained according to the method of Example 1, was placed in the reactor, and the reactor was purged with nitrogen at a flow rate of 100 mL/min. The reactor was heated to 650° C. for 10 min, and the feeding of nitrogen was stopped. Then water vapor and air were passed to the reactor for 40 min, wherein the volume ratio of water vapor to air was 1:0.1, the weight hourly space velocity of water vapor was 6 $h^{-1}$, and the weight hourly space velocity of air was 0.9 $h^{-1}$. It was determined that the coke content of the obtained catalyst is 4.7%.

The reactor was switched to be nitrogen atmosphere, the temperature therein was reduced to 490° C. and maintained for 20 min to obtain the partially regenerated catalyst, which was denoted as sample 4#.

According to reaction conditions of methanol-to-olefins in Example 1, the methanol-to-olefins reaction was performed on the partially regenerated catalyst sample 4#. The reaction time was 56 min, and the methanol conversion ratio and olefin selectivity were shown in FIG. 7.

Example 6

The deactivated catalyst A, which was obtained according to the method of Example 1, was placed in the reactor, and the reactor was purged with nitrogen at a flow rate of 100 mL/min. The reactor was heated to 600° C. for 10 min, and the feeding of nitrogen was stopped. Then water vapor and air were passed to the reactor for 30 min, wherein the volume ratio of water vapor to air was 1:0.1, the weight hourly space velocity of water vapor is 6 $h^{-1}$, and the weight hourly space velocity of air was 0.9 $h^{-1}$. It was determined that the obtained catalyst had a coke content of 5.1%.

The reactor was switched to be nitrogen atmosphere, the temperature therein was reduced to 490° C. and maintained for 20 min to obtain the partially regenerated catalyst, which was denoted as sample 5#.

According to reaction conditions of methanol-to-olefins in Example 1, the methanol-to-olefins reaction was performed on the partially regenerated catalyst sample 5#. The reaction time was 39 min, and the methanol conversion ratio and olefin selectivity were shown in FIG. 8.

Example 7

The deactivated catalyst A, which was obtained according to the method of Example 1, was placed in the reactor, and the reactor was purged with nitrogens at a flow rate of 100 mL/min. The reactor was heated to 650° C. for 10 min, and the feeding of nitrogen was stopped. Then water vapor and air were passed to the reactor for 50 min, wherein the volume ratio of water vapor to air was 1:0.06, the weight hourly space velocity of water vapor is 6 $h^{-1}$, and the weight hourly space velocity of air was 0.54 $h^{-1}$. It was determined that the obtained catalyst had a coke content of 5.9%.

The reactor was switched to be nitrogen atmosphere, the temperature therein was reduced to 490° C. and maintained for 20 min to obtain the partially regenerated catalyst, which was denoted as sample 6#.

According to reaction conditions of methanol-to-olefins in Example 1, the methanol-to-olefins reaction was performed on the partially regenerated catalyst sample 6#. The reaction time was 39 min, and the methanol conversion ratio and olefin selectivity were shown in FIG. 9.

Example 8

The deactivated catalyst A, which was obtained according to the method of Example 1, was placed in the reactor, and the reactor was purged with nitrogen at a flow rate of 100 mL/min. The reactor was heated to 550° C. for 10 min, and the feeding of nitrogen was stopped. Then water vapor and air were passed to the reactor for 90 min, wherein the volume ratio of water vapor to air was 1:0.06, the weight hourly space velocity of water vapor was 0.8 $h^{-1}$, and the weight hourly space velocity of air was 0.072 $h^{-1}$. It was determined that the obtained catalyst had a coke content of 7.5%.

The reactor was switched to be nitrogen atmosphere, the temperature therein was reduced to 490° C. and maintained for 20 min to obtain the partially regenerated catalyst, which was denoted as sample 7#.

According to reaction conditions of methanol-to-olefins in Example 1, the methanol-to-olefins reaction was performed on the partially regenerated catalyst sample 7#. The reaction time was 39 min, and the methanol conversion ratio and olefin selectivity were shown in FIG. 10.

Example 9

According to the steps and conditions in Example 6, the steps of "catalyst regeneration-methanol to olefin reaction" were repeated 10 times, and the partially regenerated catalyst obtained after 10 times of catalyst regeneration was denoted as sample 5#-10.

According to reaction conditions of methanol-to-olefin reaction in Example 1, the methanol-to-olefins reaction was performed on the partially regenerated catalyst sample 5#-10. The reaction time was 39 min, and the methanol conversion ratio and olefin selectivity were shown in FIG. 11.

Comparative Example 2

The deactivated catalyst A was placed in the reactor, and the reactor was purged with nitrogen at a flow rate of 100 mL/min. The reactor was heated to 650° C. for 10 min, and the feeding of nitrogen was stopped. Then nitrogen and air were passed to the reactor for 40 min, wherein the volume ratio of nitrogen gas to air was 1:0.1, the weight hourly space velocity of nitrogen gas was 6 $h^{-1}$, and the weight hourly space velocity of air was 0.9 $h^{-1}$. The partially regenerated catalyst obtained was denoted as sample D2#. It was determined that the coke content of sample D2# was 3.5%.

The reactor was switched to be nitrogen atmosphere, the temperature therein was reduced to 490° C. and maintained for 20 min. According to reaction conditions of methanol-to-olefins in Example 1, the methanol-to-olefins reaction was performed on the partially regenerated catalyst sample D2#. The reaction time was 72 min, and the methanol conversion ratio and olefin selectivity were shown in FIG. 12.

Example 10

Figure 13:
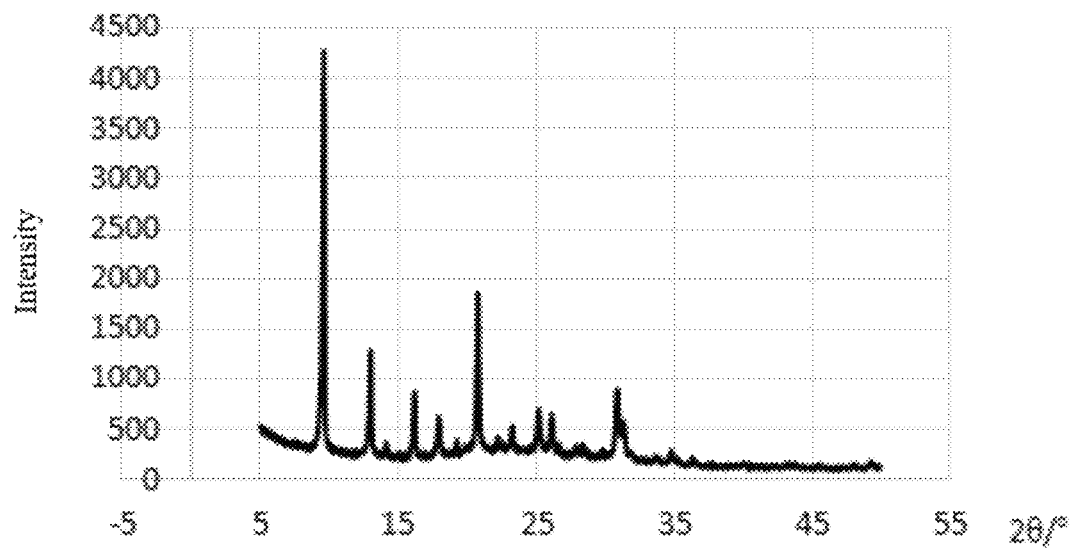
FIG. 13 shows the XRD spectra of the samples obtained according to Example 1 and Example 9 of the present application, wherein a) shows the XRD spectrum of the deactivated catalyst A obtained in Example 1; b) shows the XRD spectrum of the sample 5[#]-10 obtained in Example 9.
Figure 13:
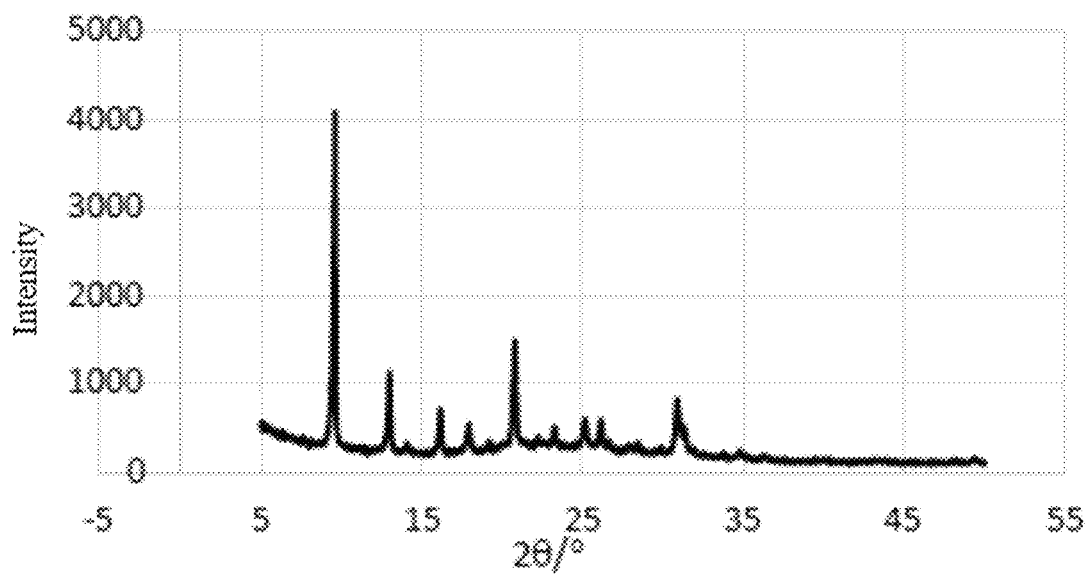

XRD was used to characterize the deactivated catalyst A and sample 5#-10. The results were shown in FIG. 13. In the XRD spectra of deactivated catalyst A (see FIG. 13a)) and sample 5#-10 (see FIG. 13b)), the peak intensity of the highest diffraction peak of sample 5#-10 was 95% of the peak intensity of the highest diffraction peak of the deactivated catalyst A.

It illustrated that, using the method for partially regenerating the catalyst described in the present application, the crystallinity of the obtained catalyst after multiple regeneration is close to that of the fresh catalyst. Thus, within the temperature range of the present application, catalyst dealumination will not occur using mixed gas of water vapor and air in certain proportion, thereby realizing the long-term recycling of the catalyst.

The conditions for partially regenerating the deactivated catalyst in Examples 2 to 9 are shown in Table 1.

TABLE 1

| Example | Sample | Regeneration temperature/ °C. | water vapor: air/v:v | weight hourly space velocity of water vapor/$h^{-1}$ | weight hourly space velocity of air /$h^{-1}$ | Regeneration time/min | Coke content of the partially regenerated catalyst/% |
|---|---|---|---|---|---|---|---|
| 2 | 1# | 650 | 1:0.4 | 8 | 4.8 | 20 | 1.2 |
| 3 | 2# | 680 | 1:0.02 | 2 | 0.06 | 180 | 1.6 |
| 4 | 3# | 620 | 1:0.14 | 3 | 0.63 | 60 | 2.8 |
| 5 | 4# | 650 | 1:0.1 | 6 | 0.9 | 40 | 4.7 |
| 6 | 5# | 600 | 1:0.1 | 6 | 0.9 | 30 | 5.1 |
| 7 | 6# | 650 | 1:0.06 | 6 | 0.54 | 50 | 5.9 |
| 8 | 7# | 550 | 1:0.06 | 0.8 | 0.072 | 90 | 7.5 |
| 9 | 5#-10 | According to the conditions in Example 6, the regeneration was repeated 10 times | | | | | |

According to the experimental results of methanol-to-olefins reaction, 3 minutes of reaction were set as the initial activity, and the catalyst activity decreased when the methanol (including dimethyl ether) conversion ratio was less than 97%. The activity maintenance time and the highest olefin selectivity before the activity decreases are important parameters of the methanol-to-olefins reaction.

Figure 2:
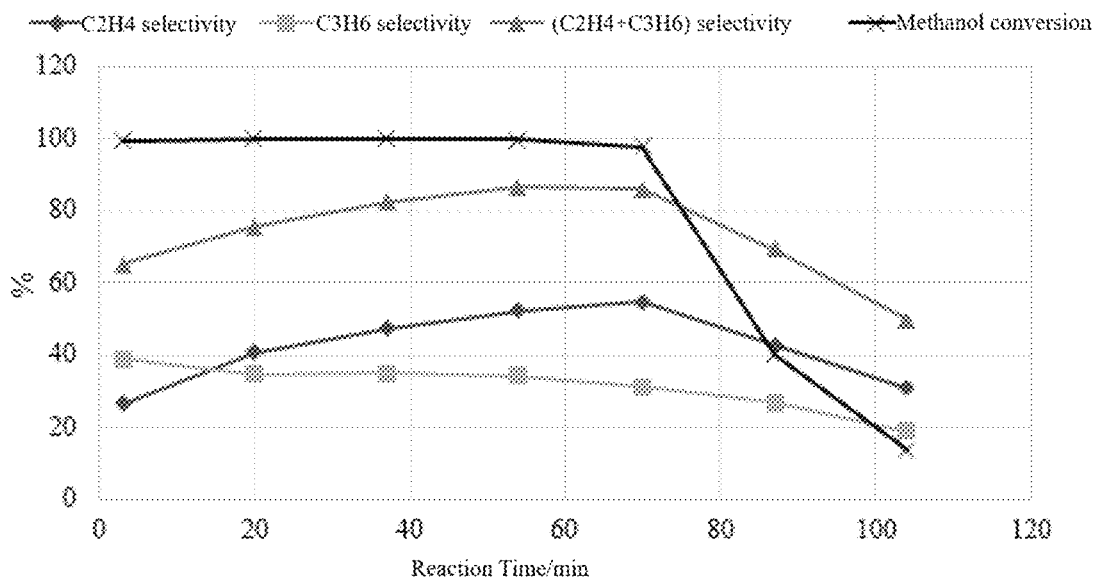
FIG. 2 is a schematic diagram showing the catalytic performance of the fresh catalyst according to Example 1 of the present application.

It can be seen from FIG. 2 that, the initial activity of the methanol-to-olefins reaction of the fresh catalyst is: the methanol conversion ratio is 99.57%, and the olefin selectivity is 65.34%. After the activity is maintained for 70 min, the methanol conversion ratio decreased significantly. After 70 min, the olefin selectivity of the fresh catalyst gradually decreases, and the highest olefin selectivity is 86.62%.

Figure 3:
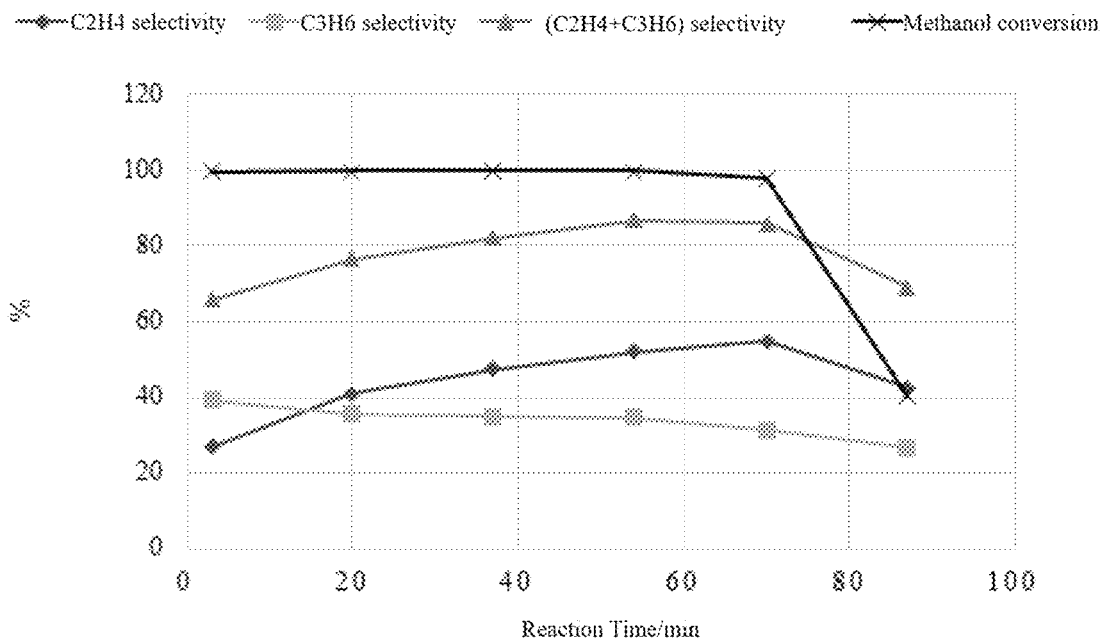
FIG. 3 is a schematic diagram showing the catalytic performance of sample D1[#] according to comparative Example 1 of the present application.

It can be seen from FIG. 3 that, with the comparative sample D1# as catalyst, the initial activity of the methanol-to-olefins reaction is: the methanol conversion ratio is 99.6%, and the olefin selectivity is 65.9%. After the activity is maintained for 70 min, the methanol conversion ratio on D1# decreases significantly. After the above reaction performs for 90 min, the methanol conversion ratio is 40%. After methanol-to-olefin reaction performs for 70 min, the olefin selectivity gradually decreases, and the highest olefin selectivity is 86.70%.

Figure 4:
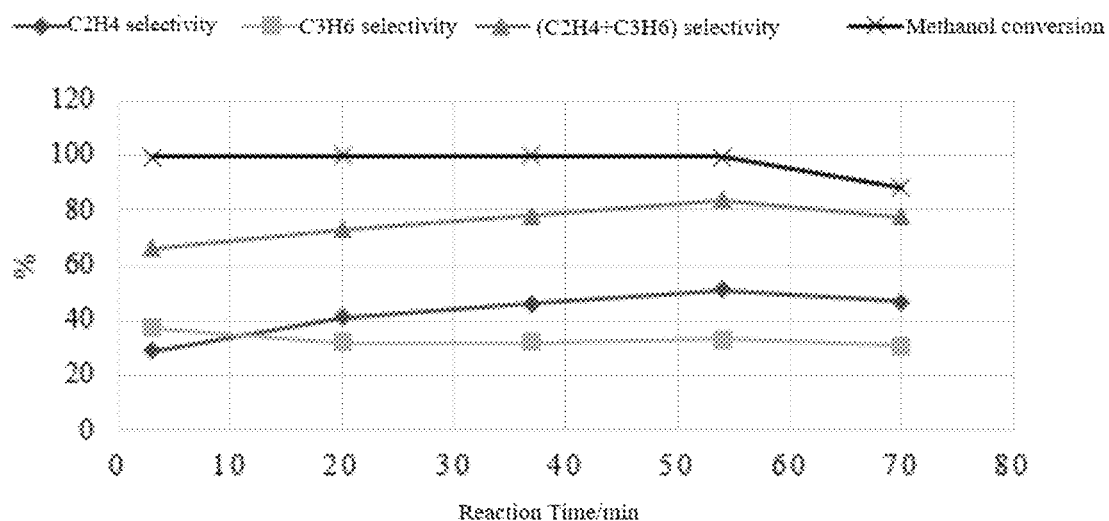
FIG. 4 is a schematic diagram showing the catalytic performance of sample 1[#] according to Example 2 of the present application.

It can be seen from FIG. 4 that, with sample 1# as catalyst, the initial activity of the methanol-to-olefins reaction is: the methanol conversion ratio was 99.5%, and the olefin selectivity was 66.2%. After the activity is maintained for about 54 min, the methanol conversion ratio decreases. The methanol conversion ratio is 85% when the above reaction performs 70 min. After the above methanol-to-olefins reaction performs for 54 min, the olefin selectivity of the catalyst gradually decreases, and the highest olefin selectivity is 84.00%. The olefin selectivity is 77.71% when the above reaction performs 70 min.

It can be seen from FIG. 5 that, with sample 2# as catalyst, the initial activity of the methanol-to-olefin reaction is: the methanol conversion ratio is 99.30%, and the olefin selectivity is 66.60%. After the activity is maintained for about 54 min, the methanol conversion ratio on the partially regenerated catalyst in Example 3 decreases. When the above reaction performs 70 min, the methanol conversion ratio is 85%. After the above methanol-to-olefin reaction performs for 54 min, the olefin selectivity of the partially regenerated catalyst gradually decreases, and the highest olefin selectivity is 85.20%. When above reaction performs about 70 min, the olefin selectivity is 78.71%.

Figure 6:
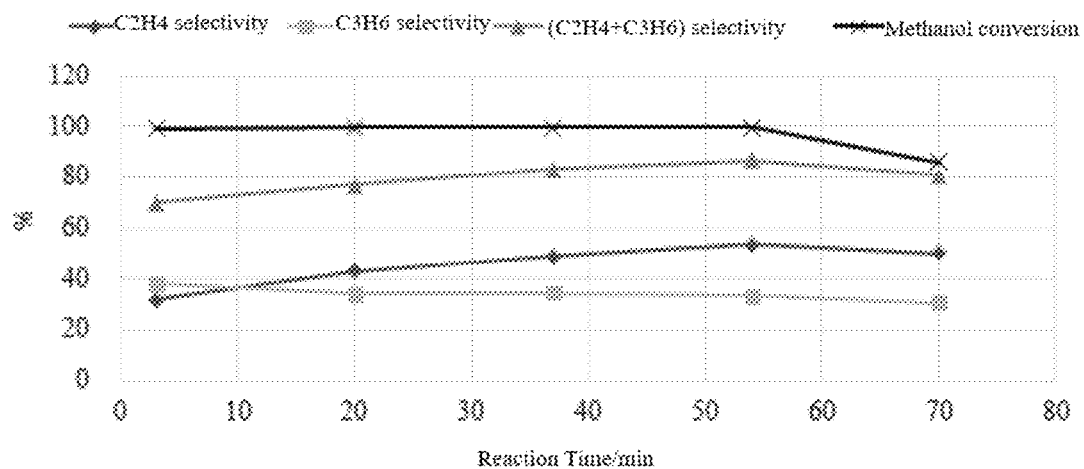
FIG. 6 is a schematic diagram showing the catalytic performance of sample 3[#] according to Example 4 of the present application.

It can be seen from FIG. 6 that, with sample 3# as catalyst, the initial activity of the methanol-to-olefin reaction is: the methanol conversion ratio is 99.43%, and the olefin selectivity is 69.95%. After the activity is maintained for about 54 min, the methanol conversion ratio on the partially regenerated catalyst in Example 4 decreases. When above reaction performs 70 min, the methanol conversion ratio is 83%. After the above methanol-to-olefin reaction performs for 55 min, the olefin selectivity of the partially regenerated catalyst gradually decreases, and the highest olefin selectivity is 87.01%. When the above reaction performs about 70 min, the olefin selectivity is 81.05%.

Figure 7:
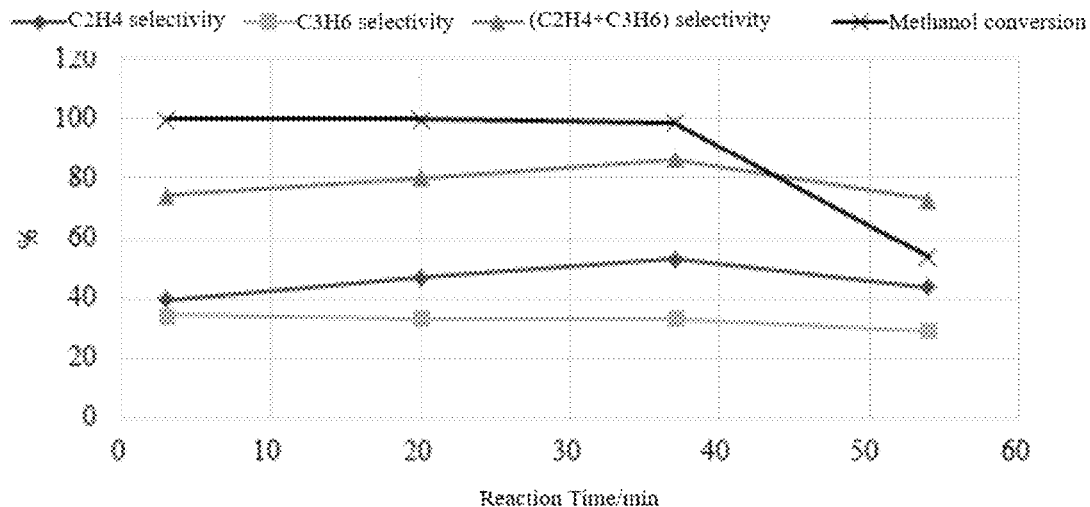
FIG. 7 is a schematic diagram showing the catalytic performance of sample 4[#] according to Example 5 of the present application.

It can be seen from FIG. 7 that, with sample 4# as catalyst, the initial activity of the methanol-to-olefin reaction is: the methanol conversion ratio is 99.67%, and the olefin selectivity is 74.26%. After the activity is maintained for about 37 min, the methanol conversion ratio on the partially regenerated catalyst in Example 5 decreases. When the above reaction performs 54 min, the methanol conversion ratio is 50%. After the above methanol-to-olefin reaction performs for 37 min, the olefin selectivity of the partially regenerated catalyst gradually decreases, and the highest olefin selectivity is 86.38%. When the above reaction performs about 54 min, the olefin selectivity is 73.05%.

Figure 8:
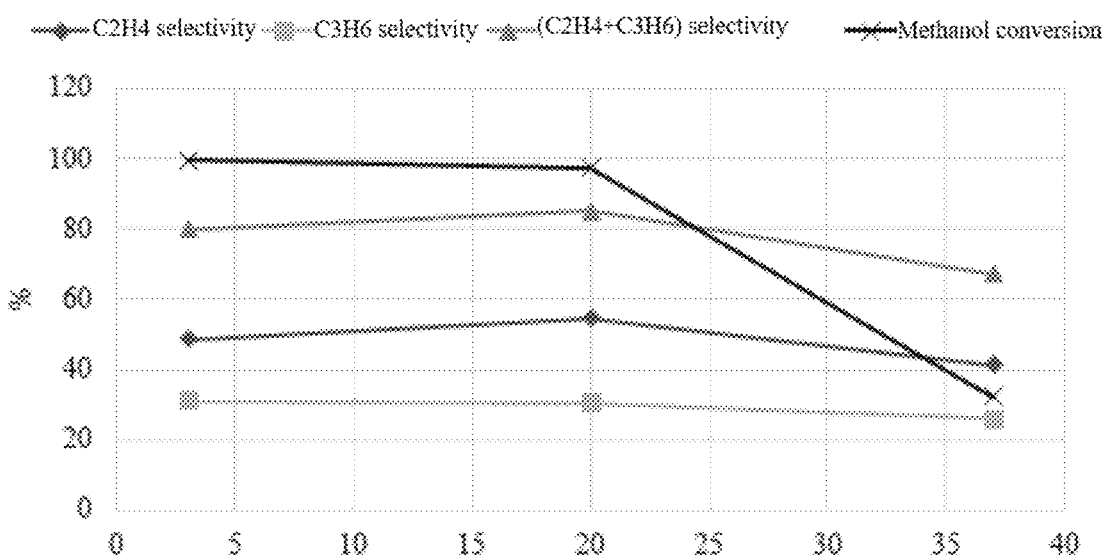
FIG. 8 is a schematic diagram showing the catalytic performance of sample 5[#] according to Example 6 of the present application.

It can be seen from FIG. 8 that, with sample 5# as catalyst, the initial activity of the methanol-to-olefin reaction is: the methanol conversion ratio is 99.73%, and the olefin selectivity is 80.01%. After the activity is maintained for about 20 min, the methanol conversion ratio on the partially regenerated catalyst in Example 6 decreases. When the above reaction performs 37 min, the methanol conversion ratio is 50%. After the above methanol-to-olefin reaction performs for 20 min, the olefin selectivity of the partially regenerated catalyst gradually decreases, and the highest olefin selectivity is 85.28%. When the above reaction performs about 37 min, the olefin selectivity is 67.47%.

Figure 9:
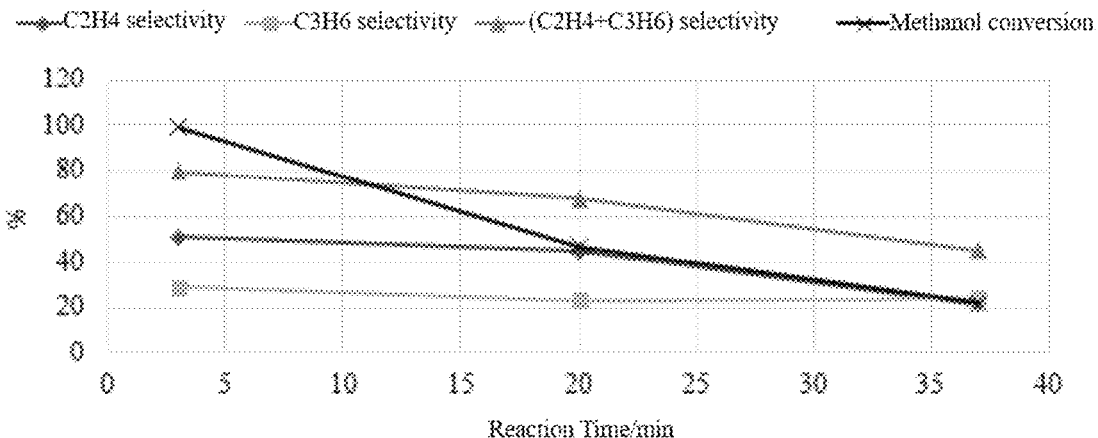
FIG. 9 is a schematic diagram showing the catalytic performance of sample 6[#] according to Example 7 of the present application.

It can be seen from FIG. 9 that, with sample 6# as catalyst, the initial activity of the methanol-to-olefin reaction is: the methanol conversion ratio is 99.72%, and the olefin selectivity is 79.74%. After the activity is maintained for about 3 min, the methanol conversion ratio on the partially regenerated catalyst in Example 7 decreases. When the above reaction performs 37 min, the methanol conversion ratio is 20%. After the above methanol-to-olefin reaction performs for 3 min, the olefin selectivity of the partially regenerated catalyst gradually decreases, and the highest olefin selectivity is 79.74%. When the above reaction performs about 37 min, the olefin selectivity is 45.2%.

Figure 10:
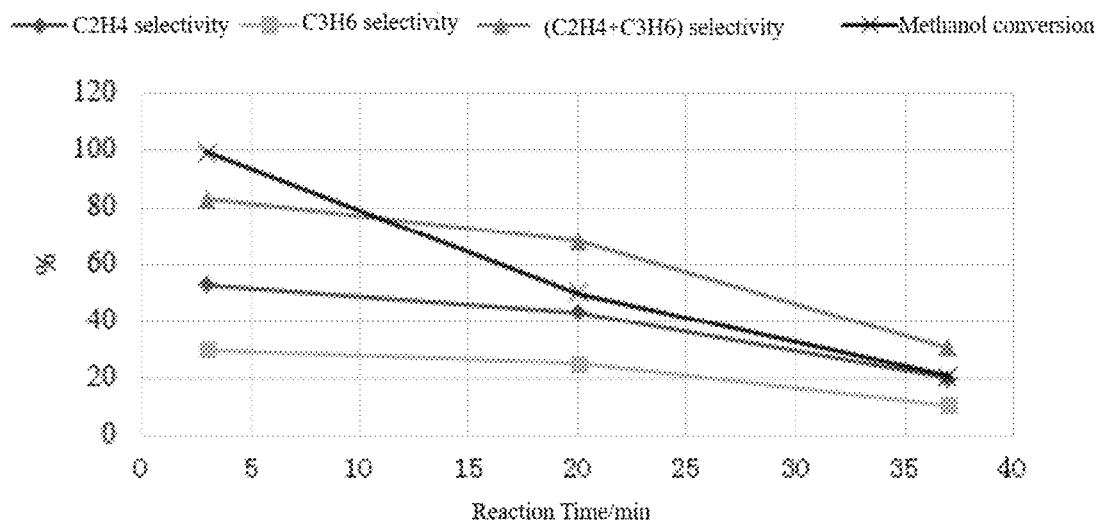
FIG. 10 is a schematic diagram showing the catalytic performance of sample 7[#] according to Example 8 of the present application.

It can be seen from FIG. 10 that, with sample 7# as catalyst, the initial activity of the methanol-to-olefin reaction is: the methanol conversion ratio is 99.47%, and the olefin selectivity is 82.97%. After the activity is maintained for about 3 min, the methanol conversion ratio on the partially regenerated catalyst in Example 8 decreases. When the above reaction performs 37 min, the methanol conversion ratio is 20%. After the above methanol-to-olefin reaction performs for 3 min, the olefin selectivity of the partially regenerated catalyst gradually decreases, and the highest olefin selectivity is 82.97%. When the above reaction performs about 37 min, the olefin selectivity is 30.72%.

Figure 11:
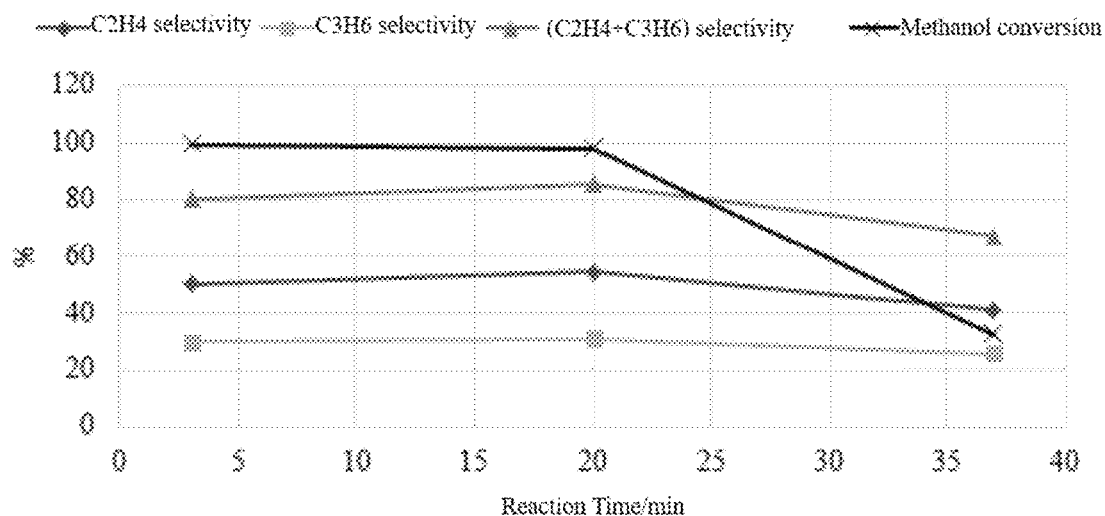
FIG. 11 is a schematic diagram showing the catalytic performance of sample 5[#]-10 according to Example 9 of the present application.

It can be seen from FIG. 11 that, with sample 5#-10 as catalyst, the initial activity of the methanol-to-olefin reaction is: the methanol conversion ratio is 99.74%, and the olefin selectivity is 80.48%. After the activity is maintained for about 20 min, the methanol conversion ratio on the partially regenerated catalyst in Example 9 decreases. When the above reaction performs 37 min, the methanol conversion ratio is 25%. After the above methanol-to-olefin reaction performs for 20 min, the olefin selectivity of the partially regenerated catalyst gradually decreases, and the highest olefin selectivity is 85.45%. When the above reaction performs about 37 min, the olefin selectivity is 67.22%.

Figure 12:
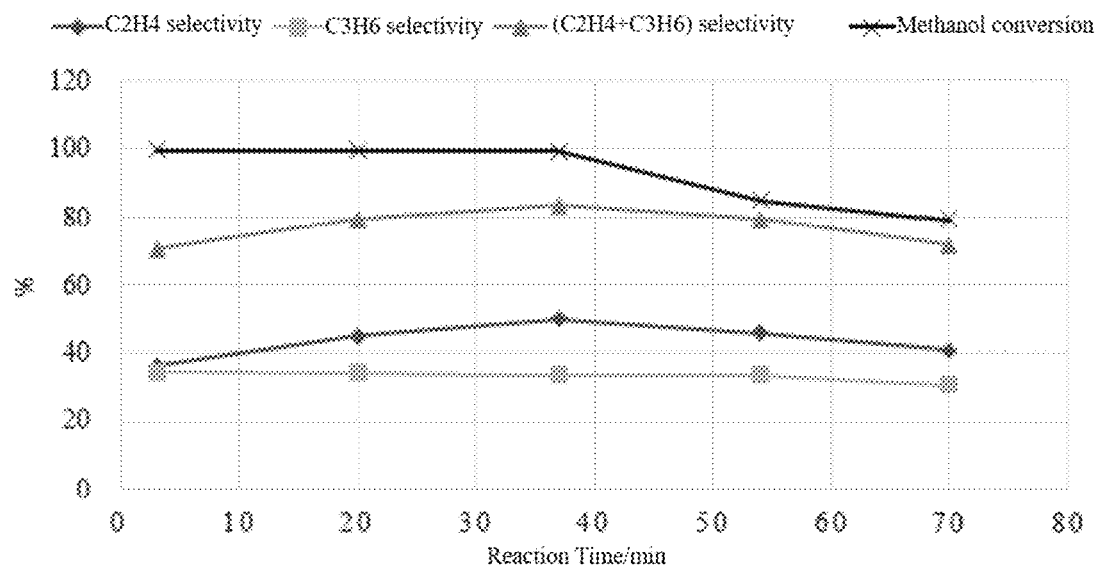
FIG. 12 is a schematic diagram showing the catalytic performance of sample D2[#] according to comparative Example 2 of the present application.

It can be seen from FIG. 12 that, the sample D2#is obtained through regeneration with a mixed gas of nitrogen gas and air as regeneration atmosphere. Using sample D2#as catalyst, the initial activity of the methanol-to-olefin reaction is: the methanol conversion ratio is 99.50%, and the olefin selectivity of 70.70%. After the activity is maintained for about 37 min, the methanol conversion ratio on the sample D2#as the partially regenerated catalyst in comparative example decreases. When the above reaction performs 54 min, the methanol conversion ratio is 85.00%. After the above methanol-to-olefin reaction performs for 37 min, the olefin selectivity of the partially regenerated catalyst gradually decreases, and the highest olefin selectivity is 83.50%. When the above reaction performs about 54 min, the olefin selectivity is 79.40%.

Comparing FIG. 2 with FIG. 3, it can be seen that the catalytic performance of the fully regenerated sample is similar to that of the fresh catalyst. Comparing FIG. 3 with FIGS. 4 to 11, it can be seen that, each of the partially regenerated catalysts for methanol and/or dimethyl ether-to-olefin, which are obtained by regeneration using a mixed gas of water vapor and air in a certain proportion according to the present application, has improved initial activity than the fully regenerated catalyst: the methanol conversion ratio is about 99% and the olefin yield has been improved, especially the ethylene selectivity has been improved even more, and the induction period has been shortened. Under suitable conditions, the highest olefin selectivity of the above partially regenerated catalysts is substantially identical to or even higher than that of fully regenerated catalyst. This is beneficial to adjust the methanol-to-olefin reaction process carried out in a circulating fluidized bed, and improves the olefin selectivity, and the produced gas after regeneration is mainly $H_2$, CO and $CH_4$, which reduces the unit consumption of methanol and improves the utilization ratio of C atoms.

Comparing FIG. 12 and FIG. 7, it can be seen, in comparison with the technical solution using a mixed gas of air and other gas as regeneration gas in the same proportion, the partially regenerated catalyst for methanol and/or dimethyl ether-to-olefin, which is obtained by regeneration using a mixed gas of water vapor and air in a certain proportion according to the present application, has higher initial olefin selectivity, and the highest olefin selectivity during the activity maintenance time. Compared with the produced $CO_2$ and CO using a mixed gas of air and other gases to regenerate the catalyst with coke deposits, the produced gas using a mixed gas of air and water vapor to regenerate the catalyst with coke deposits is mainly $H_2$, CO and $CH_4$, and thus the utilization ratio of C atoms is higher.

From the above results, it can be seen that, after partial regeneration of the catalyst for methanol and/or dimethyl ether-to-olefin with coke deposits using the mixed gas of water vapor and air, the olefin selectivity and life of the catalyst can be restored. After repeated partial regeneration, the olefin selectivity and lifetime of the partially regenerated catalyst will not be reduced or attenuated. At the same time, the XRD characterization shows that the crystallinity of the obtained catalyst after multiple regeneration is close to that of the fresh catalyst. showed that its crystallinity was close to that of the fresh catalyst, indicating that, within the temperature range of the present application, dealumination of the catalyst will not occur using mixed gas of water vapor and air, thereby realizing the long-term recycling of the catalyst.

The above examples are only illustrative, and do not limit the present application in any form. Any change or modification, made by the skilled in the art based on the technical content disclosed above, without departing from the spirit of the present application, is equivalent example and falls within the scope of the present application.

The invention claimed is:

1. A method for partially regenerating the catalyst for methanol and/or dimethyl ether-to-olefin comprising: passing a mixed gas into a regeneration zone containing a catalyst to be regenerated, and carrying out a partial regeneration reaction to obtain a regenerated catalyst;
   wherein the mixed gas comprises water vapor and air; and in the regenerated catalyst, at least a part of the regenerated catalyst has a coke content of greater than 1%;
   wherein a volume ratio of water vapor to air in the mixed gas ranges from 1:0.01 to 1:0.5;
   wherein, in the partial regeneration reaction, a contact time between the mixed gas and the catalyst to be regenerated ranges from 10 min to 200 min; and
   wherein, a space velocity of water vapor in the mixed gas passed into a regenerator ranges from 0.1 $h^{-1}$ to 10 $h^{-1}$, and a space velocity of air ranges from 0.01 $h^{-1}$ to 6 $h^{-1}$.

2. The method for partially regenerating the catalyst for methanol and/or dimethyl ether-to-olefin according to claim 1, wherein
   the volume ratio of water vapor to air in the mixed gas ranges from 1:0.01 to 1:0.14.

3. The method for partially regenerating the catalyst for methanol and/or dimethyl ether-to-olefin according to claim 1, wherein at least a part of the regenerated catalyst has a coke content ranging from 1.1% to 8%.

4. The method for partially regenerating the catalyst for methanol and/or dimethyl ether-to-olefin according to claim 1, wherein the partial regeneration reaction is carried out under a temperature ranging from 500° C. to 700° C.

5. The method for partially regenerating the catalyst for methanol and/or dimethyl ether-to-olefin according to claim 1, wherein the catalyst to be regenerated has a coke content ranging from 6% to 14%.

6. A method for methanol and/or dimethyl ether-to-olefin, which adopts fluidized bed reaction process, comprising: partially regenerating the catalyst to be regenerated using the method for partially regenerating the catalyst for methanol and/or dimethyl ether-to-olefin according to claim 1;
   wherein the method comprises the following steps:
   passing a feed gas comprising methanol and/or dimethyl ether into a fluidized bed reactor containing a catalyst for methanol-to-olefin to perform methanol-to-olefin reaction;

transporting the catalyst to be regenerated to the regeneration zone, and passing the mixed gas into the regeneration zone to perform partial regeneration reaction to obtain the regenerated catalyst; and recycling back the regenerated catalyst to the fluidized bed reactor.

7. The method for methanol and/or dimethyl ether-to-olefin according to claim 6, wherein the catalyst for methanol-to-olefin comprises silicoaluminophosphate molecular sieve.

8. The method for partially regenerating the catalyst for methanol and/or dimethyl ether-to-olefin according to claim 1, wherein at least a part of the regenerated catalyst has a coke content ranging from 2.8% to 7.5%.

9. The method for partially regenerating the catalyst for methanol and/or dimethyl ether-to-olefin according to claim 1, wherein the partial regeneration reaction is carried out under a temperature ranging from 600° C. to 680° C.

\* \* \* \* \*